United States Patent [19]

D'Ascensio et al.

[11] Patent Number: 5,108,593
[45] Date of Patent: Apr. 28, 1992

[54] APPARATUS FOR COLLECTING SUBSTANCES FLOATING IN AN EFFLUENT STREAM

[75] Inventors: Frank P. D'Ascensio, Bridgewater; Mario Graglia, Livingstone; Salvatore Mayrina, Hillside; Ronald Kumetz, Elmwood Park, all of N.J.

[73] Assignee: Passaic Valley Sewerage Commissioners, Newark, N.J.

[21] Appl. No.: 653,248

[22] Filed: Feb. 11, 1991

[51] Int. Cl.$^5$ ............................................. E04H 4/16
[52] U.S. Cl. .................................. 210/122; 210/169; 210/242.1; 4/490; 15/1.7
[58] Field of Search ............ 210/122, 169, 170, 242.1, 210/499, 538; 43/9.1; 15/1.7; 4/490

[56] References Cited

U.S. PATENT DOCUMENTS

| | | | |
|---|---|---|---|
| 3,757,953 | 9/1973 | Sky-Eagle, Jr. | 210/242.1 |
| 3,863,237 | 1/1975 | Doerr | 210/169 |
| 4,053,412 | 10/1977 | Stix | 210/169 |
| 4,089,074 | 5/1978 | Sermons | 210/169 |
| 4,518,495 | 5/1985 | Harding | 210/169 |
| 4,889,622 | 12/1989 | Newcombe-Bond | 210/169 |
| 4,994,178 | 2/1991 | Brooks | 210/169 |

Primary Examiner—Stanley S. Silverman
Assistant Examiner—Christopher Upton
Attorney, Agent, or Firm—Anthony F. Cuoco

[57] ABSTRACT

A hollow, floatable, hydrodynamically shaped member supports a screen in canopy-like fashion and is secured to a harness for being lowered into and raised from an effluent stream such as in a closed sewage system. The member floats on the stream and floating substances therein are collected by the screen for subsequent analysis or the like, as may be required for pollution control or related purposes. The harness includes a line for tethering the floatable member so that said member rises and falls with the rising and falling of the stream level. The hollow, floatable member has a removable cap, whereby ballast can be added or removed for adjusting the buoyancy thereof.

6 Claims, 3 Drawing Sheets

1

APPARATUS FOR COLLECTING SUBSTANCES FLOATING IN AN EFFLUENT STREAM

BACKGROUND OF THE INVENTION

This invention relates to apparatus arranged for floating on the surface of an effluent stream such as in a sewage system for collecting substances floating in said stream for subsequent analysis or the like, as may be required for pollution control or related purposes.

Effluent streams as in a closed sewage system must be monitored to determine the nature of substances floating in the stream. It has been found that this is best accomplished by apparatus having particular structural attributes including an arrangement which floats on the stream and is adapted for collecting the substances floating therein. The apparatus best be hydrodynamically shaped to accommodate the flow current in the effluent stream, and should include a tethering feature which permits said apparatus to rise and fall with the level of the stream. The buoyancy of the device should be adjustable, as may be required from time-to-time.

The present inventors are aware of the following prior art which relates generally to the subject matter of their invention as herein disclosed: U.S. Pat. No. 2,742,788 (Apr. 24, 1956); U.S. Pat. No. 4,166,392 (Sep. 4, 1979); U.S. Pat. No. 4,919,892 (Apr. 24, 1990); U.S. Pat. No. 4,863,692 (Sep. 5, 1989); and U.S. Pat. No. 4,863,968 (Dec. 30, 1986).

U.S. Pat. No. 2,742,778 relates to a sewer sampler featuring a pair of closely spaced screens joined at their forward ends in a point. A weir extends across the rear ends of the screens and a large container is positioned on the side of the weir opposite the screens. A narrow channel connects the screens and a container. The arrangement is disposed in a concrete chamber, and to opposite ends of which chamber inlet and outlet lines are connected. The weir extends across the chamber nearer the outlet line than the inlet line and is secured to the side walls of the chamber by angle irons or the like to which the weir is bolted and which, in turn, are bolted to the side walls of the chamber. Apparently, the apparatus is designed for a specific use, i.e. determining the loss in sewage of uranium as to which there may be requirements for inventory and accountability and is seen to be structurally different than the present invention.

U.S. Pat. No. 4,166,392 relates to an automatic water/sewer sampler. The invention features a totally immersible, rechargeable, battery powered arrangement and is constructed for suspension under water at a raw water inlet. Samples are collected in vacuum flasks apparently via suction. There is no structural equivalence between this apparatus and the present invention.

U.S. Pat. No. 4,919,892 relates to apparatus for detecting oil and other lighter than water contaminants in an effluent stream in a sewage system. The apparatus features a disposable detector which floats on the effluent stream and detects contaminants having a specific gravity lighter than the water by absorbing the contaminants in an oleophilic material, thereby permitting the contaminants to rise and collect in a collection tube. Other than the fact that the apparatus features a floatable member, there is no structural relation between the apparatus and the present invention.

U.S. Pat. No. 4,863,692 is a companion to the aforenoted U.S. Pat. No. 4,919,892 and appears to differ only in an arrangement wherein the detecting apparatus is held in a sewage system by a security system which indicates whether the detector has been tampered with since it was installed.

U.S. Pat. No. 4,631,968 relates to an effluent sampler including a collection container mounted within an effluent conduit and a dipper for periodically and automatically sampling an effluent stream. A collecting cup collects a portion of a cumulative sample for analysis. The collection container is shaped to fit within an aperture of the effluent conduit and extends both inside and outside the conduit. The dipper is mounted to the container inside the conduit for protection, and the collecting cup associated with the container is attached outside the conduit for access to the cumulative sample. The sampler includes a compressed air system for clearing the dipper and another compressed air system for intermixing the cumulative sample therewithin. There is no structural relation between this device and the present invention.

It will be readily discerned that while the prior art devices relate generally to apparatus for sampling and/or detecting substances in a sewage system and/or an effluent stream, they do not have the structural attributes of the present invention as aforenoted and do not teach the particular structural configuration herein disclosed.

SUMMARY OF THE INVENTION

This invention contemplates apparatus for collecting substances floating in an effluent stream, including a hydrodynamically shaped floatable member and a screen configured as a canopy like structure supported thereby. The floatable member is hollow and includes a capped opening through which ballast can be added or removed for adjusting the buoyancy of said member, as may be required from time-to-time. The floatable member is attached to a harness arrangement whereby the member can be lowered into and raised from the effluent stream. The harness arrangement includes a tethering line which secures the apparatus to a fixed support with sufficient slack so that the floatable member has the capability of rising and falling with the rising and falling of the effluent stream level. Alternately, the floatable member may be configured as a plurality of members in a pontoon-like arrangement for serving the purposes intended. In use, the apparatus is lowered via the harness arrangement into an effluent stream such as in a closed sewage system, whereby over a period of time substances floating in the stream accumulate on the screen and are removed therefrom for analysis or like purposes as may be required for pollution control or related purposes, upon the apparatus being raised via the harness arrangement from said stream.

DETAILED DESCRIPTION OF THE INVENTION

Figure 1:
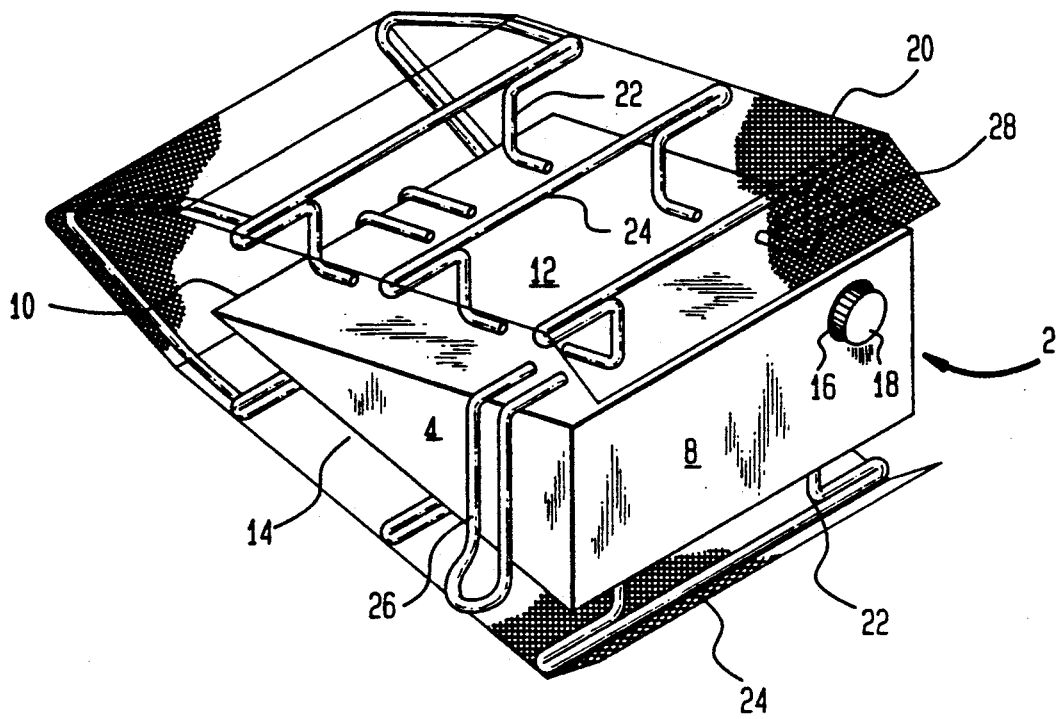
FIG. 1 is a perspective representation, showing the invention as viewed from one side thereof.
Figure 2:
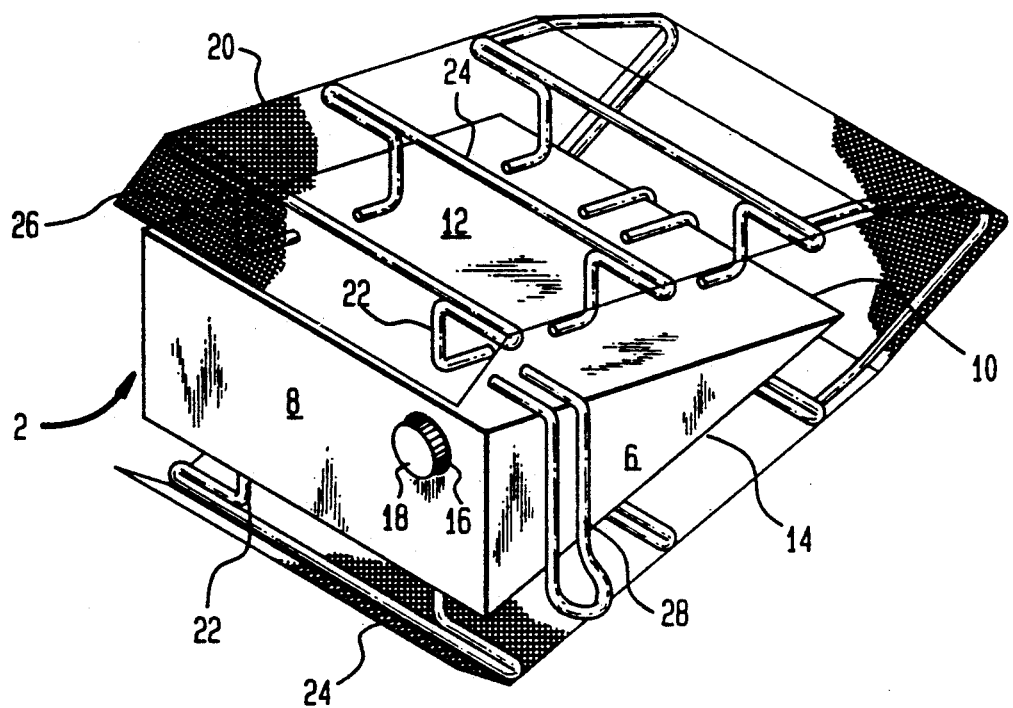
FIG. 2 is a perspective representation, showing the invention as viewed from the opposite side thereof.
Figure 3:
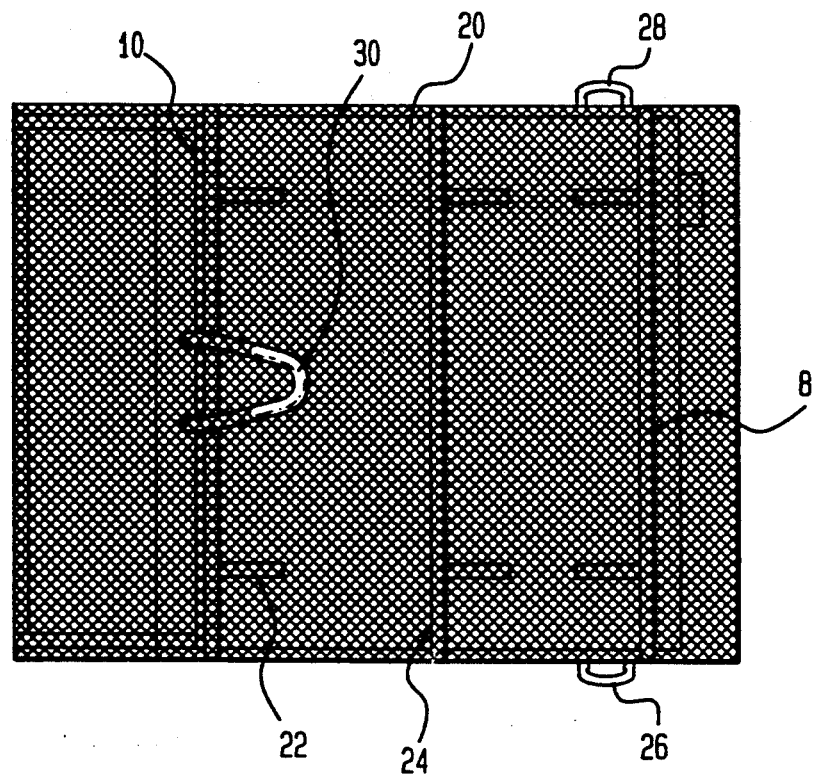
FIG. 3 is a diagrammatic top plan view representation of the invention.

With reference to FIGS. 1-3, a hollow, floatable member is designated by the numeral 2. Member 2 is formed in a hydrodynamic configuration to accommodate the flow rate in an effluent stream such as in a closed sewage system, and which flow rate has been found to be in the magnitude of one and one-half to two feet per second. Thus, member 2 is generally wedge shaped and has a pair of triangular surfaces 4 (FIG. 1) and 6 (FIG. 2) and which surfaces 4 and 6 are in parallel, spaced relation. Surfaces 4 and 6 terminate at one end in a rectangular base 8 and terminate at the opposite end in a transversely extending edge 10. A surface 12 extends angularly downwardly from one end of base 8 to edge 10 and a like surface 14 extends angularly upwardly from the opposite end of base 8 to edge 10.

Base 8 of member 2 has an orifice 16 which is normally closed by a removable cap 18. Thus, cap 18 can be removed to add or remove water or some other such ballast material from the inside of hollow member 2 to adjust its floatability or buoyancy as may be desired from time-to-time.

A screen 20 which is configured as a canopy-like structure is supported in spaced relation to surfaces 12 and 14 of member 2 by a plurality of struts or the like such as 22 which are suitably secured to said surfaces 12 and 14 and to screen 20. Screen 20 is reinforced along its length by a plurality of transversely extending ribs 24. Ribs 24 may be integral with struts 22 as shown in FIGS. 1 and 2 and may be secured to the screen. Thus, ribs 24 provide a degree of rigidity to screen 20 to best serve the purposes of the invention as will hereinafter become evident.

It will be understood that if member 2 and screen 20 are of metal, struts 22 and ribs 24 may be secured thereto as by soldering, welding, brazing, or the like. If member 2 and screen 20 are of plastic or some other such like material, the struts and ribs may be secured thereto as by cementing or the like.

It will be seen from the drawing that screen 20 is shaped to generally follow the shape of member 2, and to thus maintain the aforementioned hydrodynamic characteristics as will be understood to best serve the purposes of the invention.

A loop-like member 26 is secured to surface 12 near base 8 so as to extend transverse to side 4 beyond surface 14 (FIG. 1), and a like loop-like member 28 is likewise secured to surface 12 near base 8 so as to extend transverse to side 6 beyond surface 14 (FIG. 2). Still another loop-like member 30 is secured to member 2 near the center of edge 10 so as to extend beyond screen 20 as best shown in FIG. 3. Members 26, 28 and 30 have a purpose which will be next described.

Figure 4:
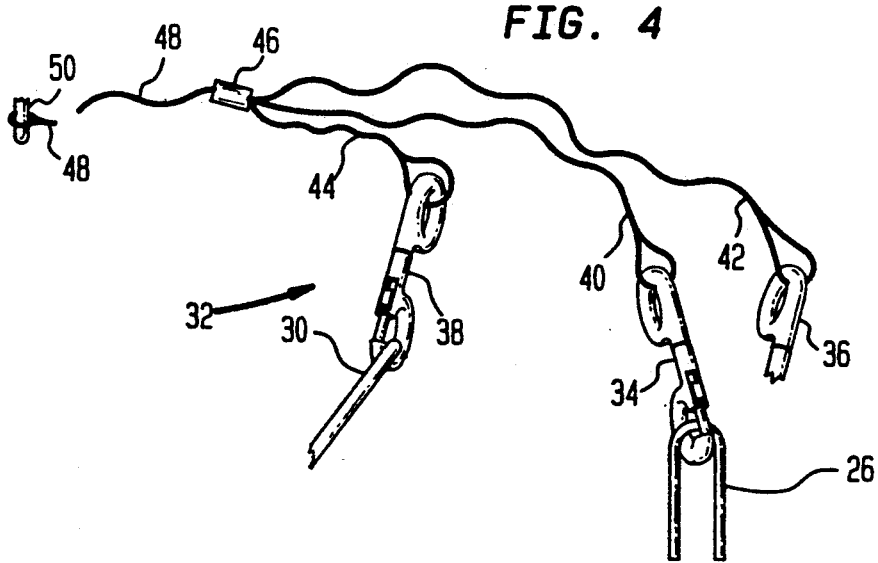
FIG. 4 is a diagrammatic representation, illustrating a harness arrangement which is attached to a floatable member in accordance with the invention.

With particular reference to FIG. 4, a harness arrangement designated generally by the numeral 32 has three like hooks such as 34, 36 and 38. Hooks 34, 36 and 38 have retractable or "snap" ends which engage loop-like members 26, 28 (not shown in FIG. 4 for purposes of simplifying the drawing) and 30, respectively. The opposite ends of hooks 34, 36 and 38 are formed as loops to retain the loop ends of lines 40, 42 and 44, respectively, and which lines may be of rope or cable or the like. The free ends of lines 40, 42 and 44 extend to a coupling member 46 from which a line 48 of substantial length extends for purposes to be hereinafter described.

In using the invention, member 2 and screen 20 supported thereby and configured as described, are lowered into an effluent stream as in a closed sewage system via harness arrangement 32 and through a previously opened manhole or the like (not otherwise shown), to allow the arrangement to float on the top of the effluent stream for a period of time. Substances floating in the stream are collected on screen 20 for sampling, analysis or such other processes as may be necessary for pollution control purposes or the like when the apparatus is raised from the stream via harness arrangement 32, the same being the intent of the invention.

In this regard, it will be noted that line 48 is used as a tethering line. That is to say, line 48 is secured to a fixed support or the like 50, with sufficient slack so that the apparatus floating on the effluent stream can rise and fall as the level of the stream rises and falls, as will be recognized as desirable.

The invention so far described considers a single floatable member 2. It will be recognized that other forms of the invention for serving the purposes intended may be desirable. One such other form is illustrated in FIG. 5.

Figure 5:
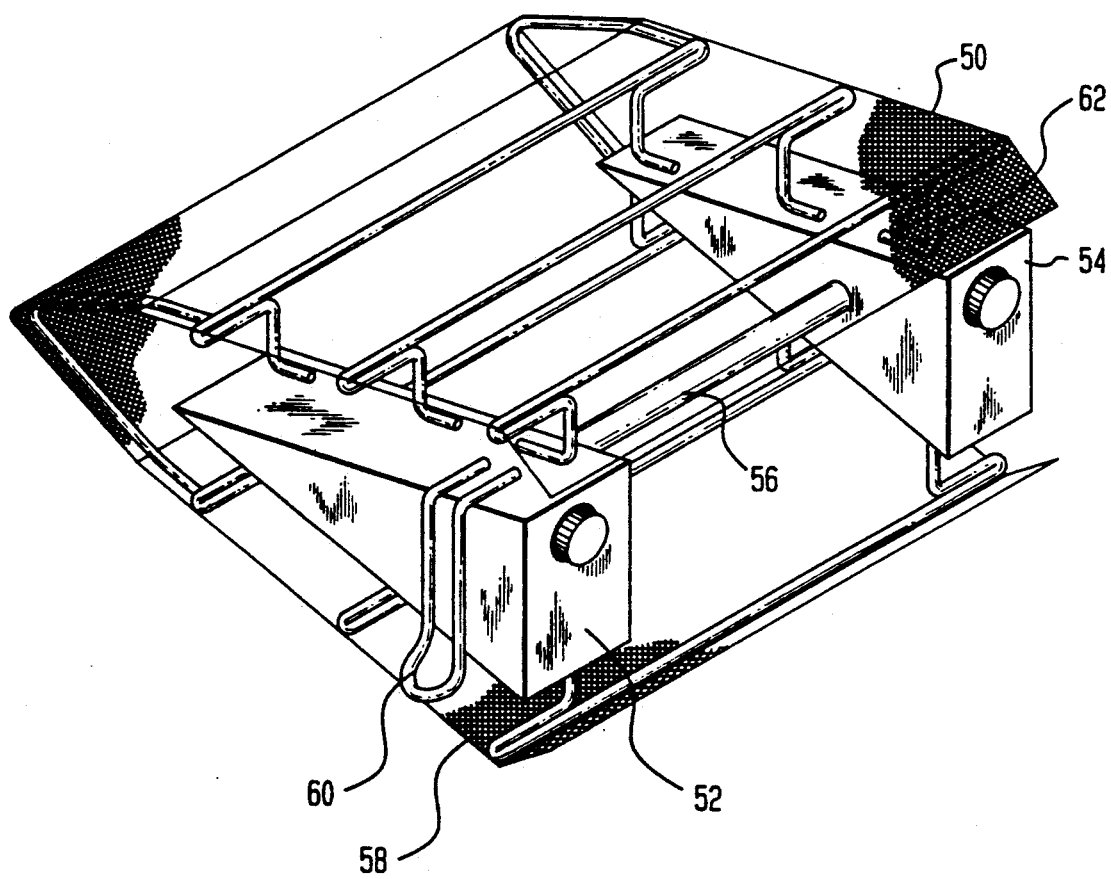
FIG. 5 is a perspective representation showing a form of the invention featuring a pontoon like arrangement for serving the purposes intended.

Thus, FIG. 5 shows the hollow floatable member of the invention as a plurality of members, shown for purposes of illustration as two in number and designated by the numerals 52 and 54. Floatable members 52 and 54 are secured together in pontoon like fashion as by a securing member 56. A screen 58 is supported in spaced relation to floatable members 52 and 54, in a manner as heretofore described with reference to FIGS. 1-3. A loop-like member 60 and a loop-like member 62 are secured to floatable members 52 and 54, respectively, near the bases thereof and a like loop-like member as members (not otherwise shown) are secured near the edges of said floatable members for engaging a harness similar to harness 32 shown in FIG. 4.

The materials to be used, the size of the apparatus and the mesh of the screen in all forms of the invention may be in accordance with particular applications as will now be understood by those skilled in the art.

There has thus been described apparatus for collecting substances floating in an effluent stream such as in a closed sewage system. A hydrodynamically shaped floatable member supports a screen in canopy-like fashion, and which screen is reinforced for purposes of rigidity. The floatable member is hollow and includes a capped opening which, when uncapped, can receive water or other like ballast for adjusting the buoyancy thereof. A harness arrangement is attached to the floatable member for lowering said member into and raising said member from the stream. The harness arrangement includes a tethering line, whereby the floatable member floats on the stream with sufficient slack so as to rise and fall with the rising and falling of the level of the effluent stream. In use, the apparatus is lowered into the stream whereby samples accumulate on the screen for analysis, sampling or such other processing as may be required for pollution control purposes. A single floatable member may be used or a plurality of floatable members arranged in pontoon-like configuration may be used, depending on the particular application involved.

With the aforenoted description of the invention in mind, reference is made to the claims appended hereto for a definition of the scope of the invention.

What is claimed is:

1. Apparatus for collecting substances floating in a flowing effluent stream, comprising:

a hollow floatable member having opposite sides and an openable end;

a plurality of supporting members fixedly disposed around the floatable member and extending away therefrom;

a screen fixedly supported by the plurality of supporting members and reinforced thereby for rigidly covering the floatable member, except at the opposite sides and the openable end thereof, in spaced relation thereto;

a plurality of loop members fixedly disposed around the floatable member;

a harness arrangement having a plurality of hook members corresponding to the plurality of loop members, each of said hook members engaging a corresponding loop member to attach the harness arrangement to the floatable member for lowering the floatable member and the screen into the stream, whereby said floatable member and said screen float in the stream, with the screen collecting substances floating in the stream, and for raising said floatable member and said screen from the stream; and said harness arrangement including a line for tethering the floatable member and the screen fixedly supported thereby with sufficient slack so that said floatable member and said screen rise and fall with the rising and falling of the level of the stream.

2. Apparatus as described by claim 1, wherein:

the floatable member is shaped to minimize resistance to the flowing of the effluent stream; and the screen fixedly supported by the plurality of supporting members is of substantially the same shape as the floatable member.

3. Apparatus as described by claim 2, wherein:

the floatable member and the screen which is of substantially the shape as the floatable member are generally wedge shaped; and a base of the wedge shaped floatable member includes an opening with a removable cap therefor, with said base thereupon being the openable end of the floatable member, and through which opening ballast is added and removed for adjusting the buoyancy of said floatable member.

4. Apparatus for collecting substances floating in a flowing effluent stream comprising:

at least two hollow floatable members, each of said members having opposite sides and an openable end;

means for attaching said floatable members each to the other in parallel spaced relation;

a plurality of supporting members fixedly arranged with the floatable members and extending away therefrom;

a screen fixedly supported by the plurality of supporting members and reinforced thereby for rigidly covering the floatable members, except at the opposite sides and the openable ends thereof;

a plurality of loop members fixed arranged with the floatable members;

a harness arrangement having a plurality of hook members corresponding to the plurality of loop members, each of said hook members engaging a corresponding loop member to attach the harness arrangement to the floatable members for lowering the attached floatable members and the screen into the stream, whereby said attached floatable members and said screen float in the stream, with the screen collecting substances floating in the stream, and for raising said attached floatable members and said screen from the stream; and said harness arrangement including a line for tethering the floatable members and the screen fixedly supported thereby with sufficient slack so that said attached floatable members and said screen rise and fall with the rising and falling of the level of the stream.

5. Apparatus as described by claim 4, wherein:

each of the floatable members is shaped to minimize resistance to the flowing of the effluent stream; and the screen fixedly supported by the plurality of supporting members is of substantially the same shape as that of the floatable members and spans the space between said members.

6. Apparatus as described by claim 5, wherein:

the floatable members and the screen which is of a shape substantially the same as that of the floatable members and spans the space between said members are generally wedge shaped; and a base of each of the wedge shaped floatable members includes an opening with a removable cap therefor, with said base thereupon being the openable end of the respective wedge shaped member, and through which openings ballast is added and removed for adjusting the buoyancy of the wedge shaped members.

* * * * *